(12) United States Patent
Wang et al.

(10) Patent No.: US 12,102,484 B2
(45) Date of Patent: Oct. 1, 2024

(54) ULTRASOUND IMAGE PROCESSING DEVICE AND METHOD, AND COMPUTER-READABLE STORAGE MEDIUM

(71) Applicants: SHENZHEN MINDRAY BIO-MEDICAL ELECTRONICS CO., LTD., Guangdong (CN); SHENZHEN MINDRAY SCIENTIFIC CO., LTD., Guangdong (CN)

(72) Inventors: Bo Wang, Shenzhen (CN); Lei Zhu, Shenzhen (CN); Xiaofeng Sui, Shenzhen (CN); Dejie Liu, Shenzhen (CN); Longfei Cong, Shenzhen (CN)

(73) Assignees: Shenzhen Mindray Bio-Medical Electronics Co., Ltd., Shenzhen (CN); Shenzhen Mindray Scientific Co., Ltd., Shenzhen (CN)

( * ) Notice: Subject to any disclaimer, the term of this patent is extended or adjusted under 35 U.S.C. 154(b) by 514 days.

(21) Appl. No.: 17/174,206

(22) Filed: Feb. 11, 2021

(65) Prior Publication Data
US 2021/0251608 A1 Aug. 19, 2021

Related U.S. Application Data

(63) Continuation of application No. PCT/CN2018/102309, filed on Aug. 24, 2018.

(51) Int. Cl.
*A61B 8/08* (2006.01)
*A61B 8/00* (2006.01)

(52) U.S. Cl.
CPC ............ *A61B 8/5207* (2013.01); *A61B 8/085* (2013.01); *A61B 8/0883* (2013.01); *A61B 8/463* (2013.01); *A61B 8/467* (2013.01)

(58) Field of Classification Search
CPC ....... A61B 8/085; A61B 8/0883; A61B 8/463; A61B 8/467; A61B 8/5207; A61B 8/5223
See application file for complete search history.

(56) References Cited

U.S. PATENT DOCUMENTS

| 10,376,236 B2 | 8/2019 | Abe | |
|---|---|---|---|
| 2007/0258631 A1* | 11/2007 | Friedman | G16H 40/63 382/128 |

(Continued)

FOREIGN PATENT DOCUMENTS

| CN | 102930555 A | 2/2013 |
|---|---|---|
| CN | 105407811 A | 3/2016 |

(Continued)

OTHER PUBLICATIONS

English Translation of Foreign Yamauchi JP 4614548 (Year: 2010).*

(Continued)

*Primary Examiner* — Joseph M Santos Rodriguez
*Assistant Examiner* — Brooke Lyn Klein
(74) *Attorney, Agent, or Firm* — Sheppard Mullin Richter & Hampton LLP (57) ABSTRACT

An ultrasound image processing device and a method for quantitative analysis of cardiac motion are provided. The device comprises: a display; and a processor configured to: obtain an ultrasound presentation, wherein the ultrasound presentation comprises one of an ultrasound image and an ultrasound video; perform a motion tracking on at least one region of interest according to the ultrasound presentation to obtain a tracking result of the at least one region of interest; determine a tracking quality of the tracking result of the at least one region of interest; and control the display to display the tracking quality of the at least one region of interest, wherein the tracking quality is a confidence of the tracking result of the corresponding region of interest and indicates a (Continued)

credibility of the tracking result of the corresponding region of interest.

16 Claims, 6 Drawing Sheets

(56) References Cited

U.S. PATENT DOCUMENTS

| | | | | |
|---|---|---|---|---|
| 2010/0022880 | A1* | 1/2010 | Sathyanarayana | ............................ A61B 5/02007 600/443 |
| 2010/0249591 | A1* | 9/2010 | Heimdal | ................. G06T 19/00 600/443 |
| 2014/0088424 | A1* | 3/2014 | Noguchi | .............. A61B 8/5284 600/440 |
| 2015/0265248 | A1* | 9/2015 | Jin | ......................... A61B 8/469 600/440 |
| 2016/0113632 | A1 | 4/2016 | Ribes et al. | |
| 2016/0287215 | A1* | 10/2016 | Choi | .................... A61B 8/5207 |
| 2017/0181730 | A1 | 6/2017 | Ardon et al. | |
| 2018/0116635 | A1 | 5/2018 | Dufour et al. | |
| 2018/0214129 | A1 | 8/2018 | Dufour et al. | |

FOREIGN PATENT DOCUMENTS

| | | | |
|---|---|---|---|
| CN | 106408591 A | 2/2017 | |
| CN | 106659473 A | 5/2017 | |
| JP | 4614548 B2 * | 1/2011 | ......... G06F 19/3437 |
| WO | 2006/013481 A1 | 2/2006 | |
| WO | 2014/080833 A1 | 5/2014 | |

OTHER PUBLICATIONS

PCT International Search Report and the Written Opinion mailed May 29, 2019, issued in related International Application No. PCT/CN2018/102309, with partial English translation (9 pages).

PCT International Preliminary Report on Patentability mailed Mar. 11, 2021, issued in related International Application No. PCT/CN2018/102309, with English translation (10 pages).

First Search dated Feb. 20, 2022, issued in related Chinese Application No. 201880096110.9 (2 pages).

* cited by examiner

FIG. 8

ULTRASOUND IMAGE PROCESSING DEVICE AND METHOD, AND COMPUTER-READABLE STORAGE MEDIUM This application is a continuation application of International Patent Application No. PCT/CN2018/102309, filed with the China National Intellectual Property Administration (CNIPA) on Aug. 24, 2018. The content of the above application is incorporated herein by reference in its entirety.

TECHNICAL FIELD

The disclosure relates to a device, and in particular to an ultrasound image processing device, and a ultrasound image processing method using the ultrasound image processing device.

BACKGROUND

At present, an ultrasound imaging technology has been widely applied in the medical field, and has also been widely applied in the diagnosis of cardiovascular diseases. With the continuous development of cardiovasology, which is an important branch discipline of clinical medicine, methods for diagnosis of cardiovascular diseases, whether noninvasive or invasive, have constantly emerged and been replaced or improved. Ultrasound cardiogram is a method developed to diagnose cardiovascular diseases in the 1950s. An ultrasound imaging technology is a noninvasive imaging technology, which is easy and simple to operate, has strong repeatability, not only may display anatomical images of the heart and large blood vessels, but also may observe physiological activities of the heart and large blood vessels in real time, providing valuable diagnostic data. Thus, the technology has attracted much attention of clinicians, and has been continuously popularized and applied. Over the past 50 years, the ultrasound cardiogram technology has developed rapidly, starting from an M-mode ultrasound cardiogram to a two-dimensional ultrasound cardiogram, a transesophageal ultrasound cardiogram, etc. Techniques for quantitative analysis of cardiac motion have also emerged, including Doppler ultrasound cardiogram technology (TDI) as well as speckle tracking based on B-ultrasound images, both of which have their own drawbacks.

The Doppler ultrasound cardiogram technology may be used to detect the motion velocity of tissues in the direction of an acoustic beam by using the principle of Doppler frequency shift, providing an effective means for analysis of cardiac motion. Due to the limitation of Doppler principle, the Doppler ultrasound cardiogram technology cannot accurately acquire the information of the heart in an imaging plane, such as two-dimensional velocity information, so it is limited in application.

The speckle tracking based on B-ultrasound images tracks the motion of myocardial tissue by tracking speckles formed by echo signals of the cardiac tissue on the B-ultrasound images, and the technology may obtain the two-dimensional motion of the cardiac tissue in the imaging plane and may be applied to various sections of heart views.

However, the accuracy of quantitative analysis of cardiac motion based on speckle tracking is directly affected by tracking accuracy. For the two-dimensional ultrasound cardiogram, local signal defects sometimes appear under the influence of imaging conditions such as an acoustic window, noises and artifacts would seriously affect a tracking algorithm, resulting in the problem of inaccurate local tracking. Certainly, analysis parameters obtained in this case are not credible. Therefore, the visual and comprehensive evaluation of the tracking quality, that is, the confidence of the analysis parameters, plays a crucial role in a quantitative analysis system, and affects the application of this technology in clinical and scientific research fields to a large extent.

In consequence, although the existing ultrasound imaging technologies may qualitatively provide an effective or ineffective judgment of local tracking, only an effective or ineffective qualitative result may be provided, and an effective or ineffective judgment rule and threshold is insufficient for a user to control and understand why the result is effective or ineffective; and the result may be seen only at the time of current analysis, and a macroscopic connection cannot be conveniently established. For example, regions affected in a complete cardiac structure, coronary artery conditions corresponding to the structure, etc. are not visually enough, so it is difficult for the user to actually get help from them.

SUMMARY

The disclosure provides an ultrasound image processing device and a method for quantitative analysis of cardiac motion, which may indicate the quantified confidence of a tracking result and provide more objective evaluation for the tracking result.

In an embodiment, provided is an ultrasound image processing device, comprising: a display; and a processor configured to execute the following steps: an ultrasound presentation is acquired, wherein the ultrasound presentation comprises either one of an ultrasound image and an ultrasound video; motion tracking is performed on at least one region of interest according to the ultrasound presentation to obtain a tracking result of the at least one region of interest; a tracking quality of the tracking result of the at least one region of interest is determined; and the display is controlled to display the tracking quality of the at least one region of interest, wherein the tracking quality is the confidence of a tracking result of a corresponding region of interest and indicates the credibility of the tracking result of the corresponding region of interest.

In an embodiment, the step that "a tracking quality of the tracking result of the at least one region of interest is determined" comprises: the tracking qualities of a plurality of local sub-regions are respectively determined according to the plurality of local sub-regions formed by dividing the region of interest in advance.

In an embodiment, the step that "the display is controlled to display the tracking quality of the at least one region of interest" comprises: tracking quality indicators of the local sub-regions are generated according to the tracking qualities of the local sub-regions of the region of interest; in combination with an anatomical structure of the region of interest and the plurality of local sub-regions divided in advance, the tracking quality indicators of the plurality of local sub-regions of the region of interest are arranged in an anatomical shape of the region of interest in the form of color coding; wherein the tracking quality indicator of each local sub-region corresponds to a color coded block; and the display is controlled to display the tracking quality indicators arranged in the anatomical shape of the region of interest.

In an embodiment, the step that "the display is controlled to display the tracking quality of the at least one region of interest" further comprises: the display is controlled to display a quality standard reference indicator; and the quality standard reference indicator is provided to determine the tracking qualities indicated by the tracking quality indicators.

In an embodiment, the ultrasound image processing device further comprises an input unit, and the processor is further configured to discard an analysis result of one or more local sub-regions to be deleted in response to an action of deleting the local sub-region that is input by a user through the input unit.

In an embodiment, the processor is further configured to execute the following steps: the display is controlled to generate a prompt message to prompt the user whether to accept the tracking result; and if the user selects "Yes", the display is controlled to display an analysis result.

In an embodiment, the anatomical shape formed by arranging the tracking quality indicators of the plurality of local sub-regions is a shape of a cardiac segmented diagram and/or a shape of a bull's eye plot.

In an embodiment, the processor is further configured to execute the following steps: the parts of the anatomical shape corresponding to the selected local sub-regions are highlighted in response to local sub-regions of a target region of interest selected by a user.

In an embodiment, the tracking result includes at least a quantitative parameter of myocardial motion.

In an embodiment, the ultrasound image processing device further comprises a memory, and the processor is configured to acquire, from the memory, the ultrasound presentation collected and stored in advance.

In an embodiment, the ultrasound image processing device further comprises an ultrasound presentation collecting apparatus configured to collect an ultrasound presentation, and the processor is configured to obtain the ultrasound presentation collected by the ultrasound presentation collecting apparatus.

In an embodiment, the ultrasound presentation collecting apparatus comprises: a probe; a transmitting circuit configured to excite the probe to transmit an ultrasound wave to the region of interest; and a receiving circuit configured to receive an echo of the ultrasound wave to obtain an echo signal, wherein the processor processes the echo signal to obtain the ultrasound presentation.

In an embodiment, the at least one region of interest comprises at least one of an endocardium, a midmyocardium, and an epicardium.

In an embodiment, provided is an ultrasound image processing method, comprising: an ultrasound presentation is acquired, wherein the ultrasound presentation comprises either one of an ultrasound image and an ultrasound video; motion tracking is performed on at least one region of interest according to the ultrasound presentation to obtain a tracking result of the at least one region of interest; a tracking quality of the tracking result of the at least one region of interest is determined; and the tracking quality of the at least one region of interest is displayed, wherein the tracking quality is the confidence of a tracking result of a corresponding region of interest and indicates the credibility of the tracking result of the corresponding region of interest.

In an embodiment, the step that "a tracking quality of the tracking result of the at least one region of interest is determined" comprises: the tracking qualities of a plurality of local sub-regions are respectively determined according to the plurality of local sub-regions formed by dividing the region of interest in advance.

In an embodiment, the step that "the tracking quality of the at least one region of interest is displayed" comprises: tracking quality indicators of the local sub-regions are generated according to the tracking qualities of the local sub-regions of the region of interest; in combination with an anatomical structure of the region of interest and the plurality of local sub-regions divided in advance, the tracking quality indicators of the plurality of local sub-regions of the region of interest are arranged in an anatomical shape of the region of interest in the form of color coding; wherein the tracking quality indicator of each local sub-region corresponds to a color coded block; and the tracking quality indicators arranged in the anatomical shape of the region of interest are displayed.

In an embodiment, the step that "the tracking quality of the at least one region of interest is displayed" further comprises: a quality standard reference indicator is displayed, wherein the quality standard reference indicator is provided to determine tracking qualities indicated by the tracking quality indicators.

In an embodiment, the method further comprises a step: an analysis result of a certain local sub-region to be deleted is discarded in response to an action of deleting the local sub-region by a user.

In an embodiment, the method further comprises a step: a prompt message is generated to prompt the user whether to accept the tracking result; and if the user selects "Yes", an analysis result is displayed.

In an embodiment, the anatomical shape formed by arranging the tracking quality indicators of the plurality of local sub-regions is a shape of a cardiac segmented diagram and/or a shape of a bull's eye plot.

In an embodiment, the method further comprises a step: the parts of the anatomical shape corresponding to the selected local sub-regions are highlighted in response to local sub-regions of a target region of interest selected by a user.

In an embodiment, the tracking result includes at least a quantitative parameter of myocardial motion.

In an embodiment, the step that "an ultrasound presentation is acquired" comprises: an ultrasound presentation is collected and acquired in real time by an ultrasound presentation collecting apparatus, or the ultrasound presentation collected and stored in advance is acquired from a memory or other device.

In an embodiment, the at least one region of interest comprises at least one of an endocardium, a midmyocardium, and an epicardium.

In an embodiment, provided is a computer-readable storage medium storing a plurality of program instructions, the plurality of program instructions being configured to be invoked by a processor to execute any one of the methods described above.

According to the ultrasound image processing device, the method for quantitative analysis of cardiac motion and the computer-readable storage medium of the disclosure, quantified confidence is provided to indicate whether a tracking result is credible or not, so that the user can determine more accurately whether the tracking result is qualified or unqualified according to other factors, and further, the tracking qualities may be illustrated vividly and displayed more visually according to the anatomical structure.

BRIEF DESCRIPTION OF THE DRAWINGS

In order to illustrate the technical solutions in the embodiments of the disclosure more clearly, a brief introduction to the drawings required for the embodiments will be provided below. Obviously, the drawings in the following description are merely some of the embodiments of the disclosure, and those of ordinary skill in the art would also obtain other drawings according to these drawings without involving any inventive effort.

DESCRIPTION OF THE PREFERRED EMBODIMENTS

The technical solutions of the embodiments of the disclosure will be described below clearly and comprehensively in conjunction with the drawings of the embodiments of the disclosure. Obviously, the embodiments described are merely some, rather than all, of the embodiments of the disclosure. Based on the embodiments given in the disclosure, all other embodiments that would be obtained by those of ordinary skill in the art without involving any inventive effort shall all fall within the scope of protection of the disclosure.

Figure 1:
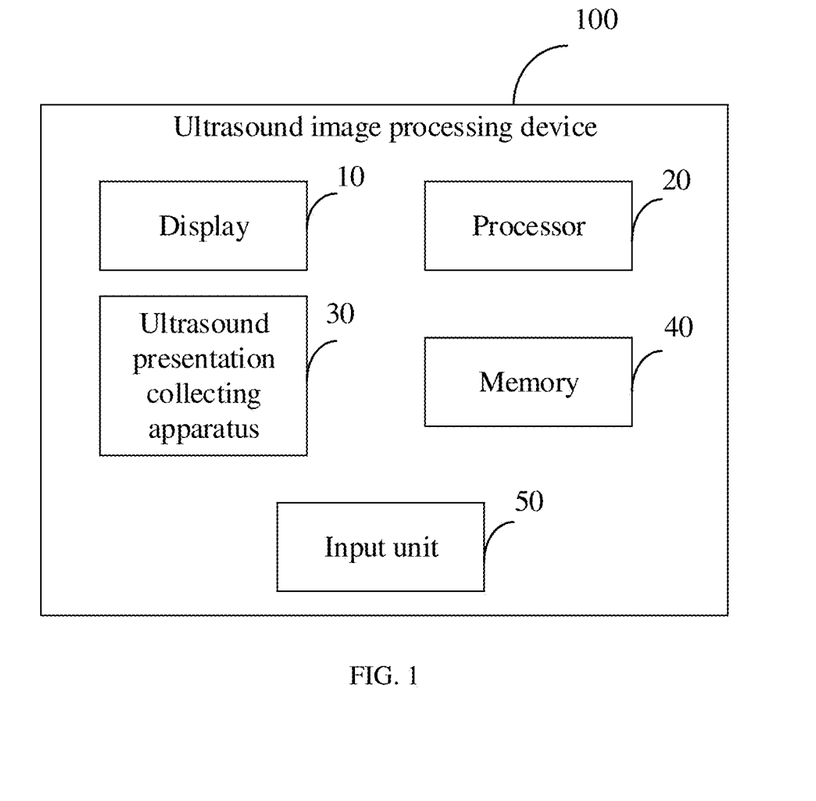
FIG. 1 is a structural block diagram of an ultrasound image processing device in an embodiment of the disclosure.

Referring to FIG. 1, a structural block diagram of an ultrasound image processing device 100 in an embodiment of the disclosure is shown. The ultrasound image processing device 100 comprises a display 10 and a processor 20. The processor 20 is configured to acquire an ultrasound presentation, and the ultrasound presentation includes either one of an ultrasound image and an ultrasound video. The ultrasound presentation is obtained by performing ultrasound scanning on at least one region of interest.

The processor 20 is also configured to perform motion tracking, through speckle tracking, on at least one region of interest in a heart according to the ultrasound presentation to obtain a tracking result of the at least one region of interest, and a tracking quality of the tracking result of the at least one region of interest is determined.

The processor 20 is further configured to control the display 10 to display the tracking quality of the at least one region of interest after the tracking is completed, wherein the tracking quality is the confidence of a tracking result of a corresponding region of interest, indicating the credibility of the tracking result of the corresponding region of interest.

That is, the tracking quality shows the quantified credibility of the tracking result, for example, the credibility is eighty percent, etc.

Therefore, in the application, what is used to reflect the quality of the tracking result is the confidence of the tracking result, not just a simple qualified or unqualified determination result, so that a user can determine more accurately whether the tracking result is qualified or unqualified according to other factors.

As shown in FIG. 1, the ultrasound image processing device 100 further comprises an ultrasound presentation collecting apparatus 30, and the ultrasound presentation collecting apparatus 30 is configured to collect an ultrasound presentation. The processor 20 is connected to the ultrasound presentation collecting apparatus 30. In some embodiments, the ultrasound presentation acquired by the processor 20 is the ultrasound presentation collected by the ultrasound presentation collecting apparatus 30.

Figure 2:
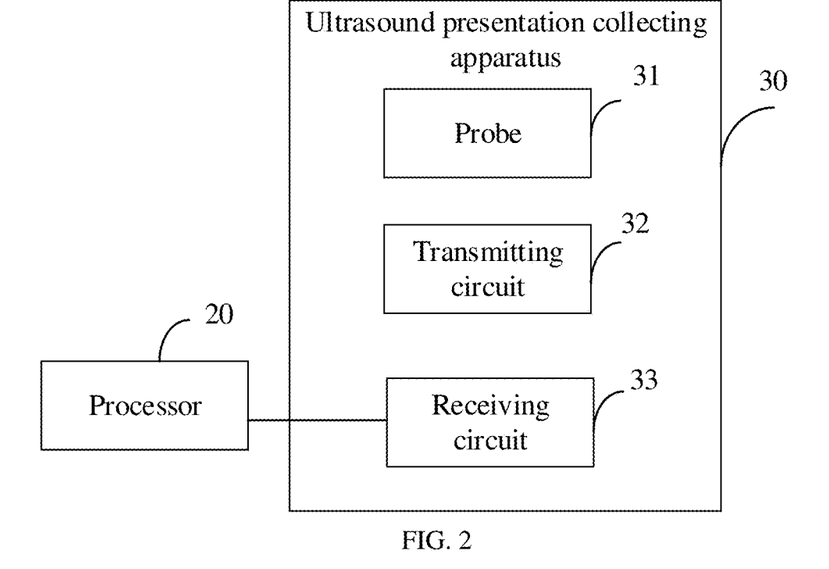
FIG. 2 is a schematic structural diagram of an ultrasound presentation collecting apparatus in an ultrasound image processing device in an embodiment of the disclosure.

Referring also to FIG. 2, a schematic structural diagram of the ultrasound presentation collecting apparatus 30 is shown. As shown in FIG. 2, the ultrasound presentation collecting apparatus 30 comprises a probe 31, a transmitting circuit 32 and a receiving circuit 33. The transmitting circuit 32 is configured to excite the probe 31 to transmit an ultrasound wave to at least one region of interest in a heart. The receiving circuit 33 is configured to receive an echo of the ultrasound wave to obtain an echo signal. The echo signal may be sent to the processor 20, and the processor 20 may process the echo signal to obtain the ultrasound presentation.

As shown in FIG. 1, the ultrasound image processing device 100 further comprises a memory 40, and the ultrasound presentation is stored in the memory 40. The processor 20 is also connected to the memory 40, and in some embodiments, the processor 20 obtains the ultrasound presentation from the memory 40. Obviously, in other embodiments, the processor 20 may also be connected to other devices so as to obtain the ultrasound presentation from other devices. For example, the processor 20 may also be in communication connection with a server to download a desired ultrasound presentation from the server.

The process in which the processor 20 determines the tracking quality of the tracking result of the at least one region of interest comprises: the processor 20 determines the tracking quality of each local sub-region of each region of interest according to a plurality of local sub-regions formed by dividing each region of interest in advance.

Figure 3:
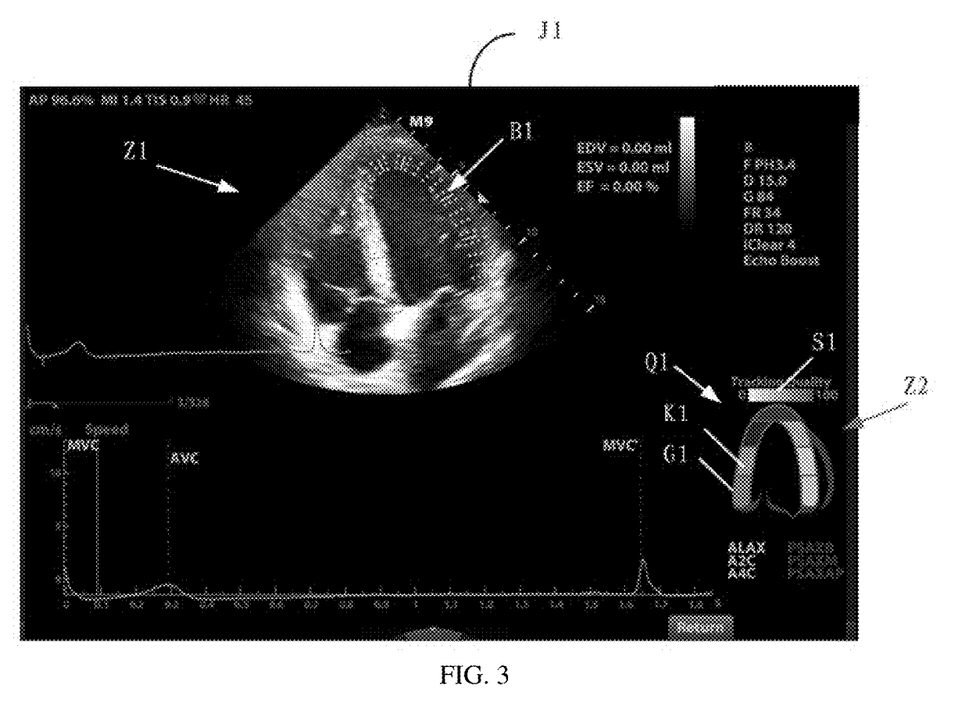
FIG. 3 is a schematic diagram of a tracking determination interface in an embodiment of the disclosure.

Referring also to FIG. 3, a schematic diagram of a tracking determination interface J1 displaying tracking quality is shown. The tracking quality of the at least one region of interest comprises a tracking quality indicator G1 of a local sub-region of each region and a quality standard reference indicator S1. The process in which the processor 20 controls the display 10 to display the tracking quality of the at least one region of interest after the tracking is completed comprises: the processor 20 generates the tracking quality indicator G1 of each local sub-region according to the tracking quality of each local sub-region of each region of interest, and in combination with a cardiac anatomical structure of each region of interest and the plurality of local sub-regions divided in advance, the tracking quality indicators G1 of the plurality of local sub-regions of each region of interest are arranged in an anatomical shape of the region of interest in the form of color coding, wherein the tracking quality indicator G1 of each local sub-region corresponds to a color coded block K1; and the processor 20 also controls the display 10 to display the tracking quality indicators G1 arranged in the anatomical shape of the region of interest, and controls the display 10 to display the quality standard reference indicator S1, and the quality standard reference indicator S1 is provided to determine the tracking qualities indicated by the tracking quality indicators.

Figure 4:
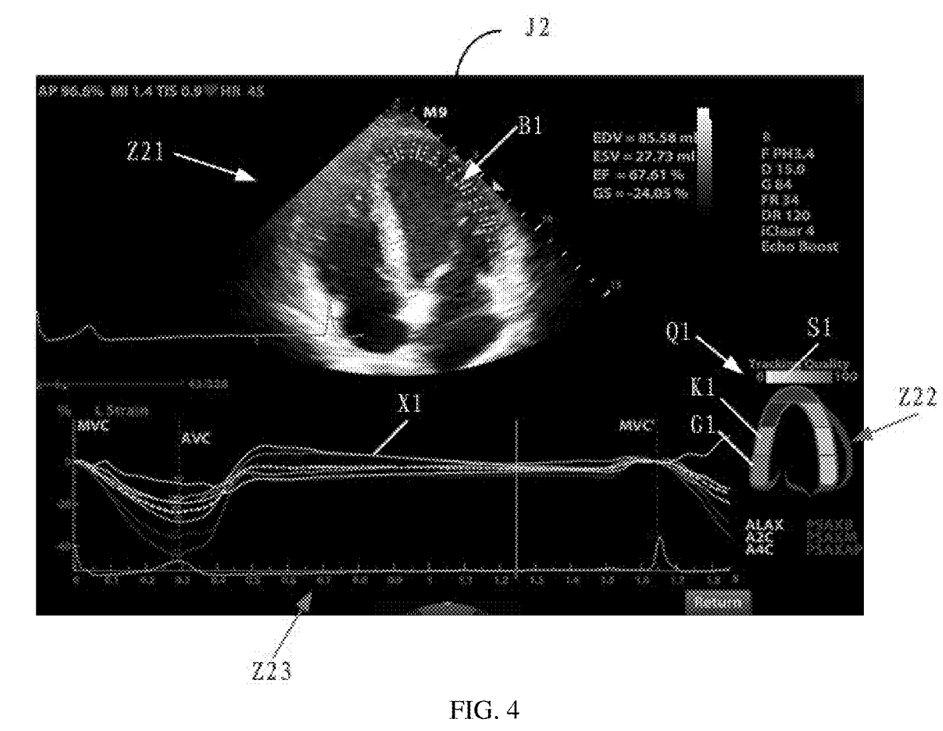
FIG. 4 is a schematic diagram of an analysis result interface in an embodiment of the disclosure.
Figure 5:
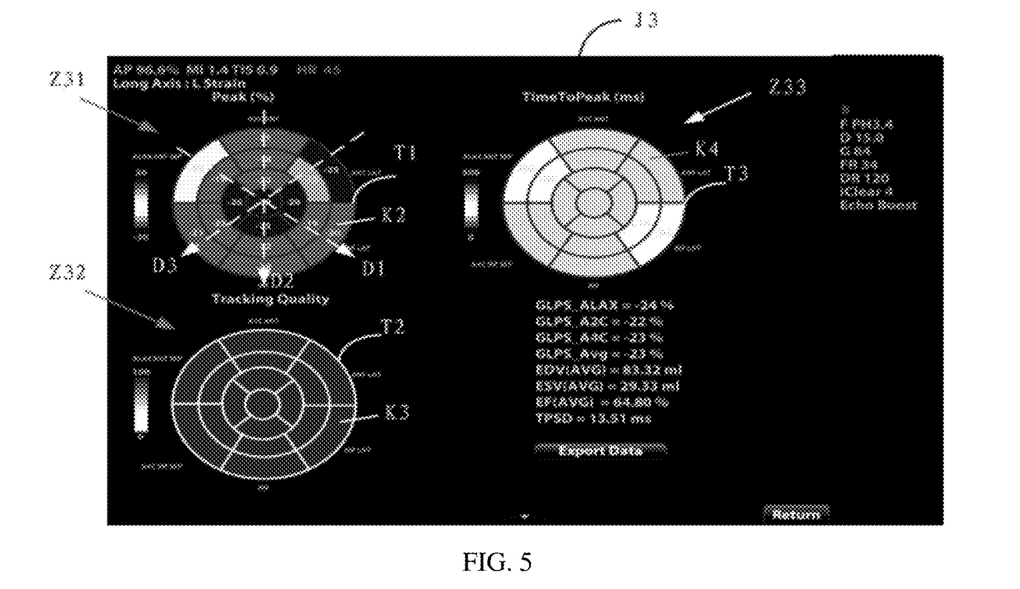
FIG. 5 is a schematic diagram of a bull's eye plot display interface in an embodiment of the disclosure.
Figure 6:
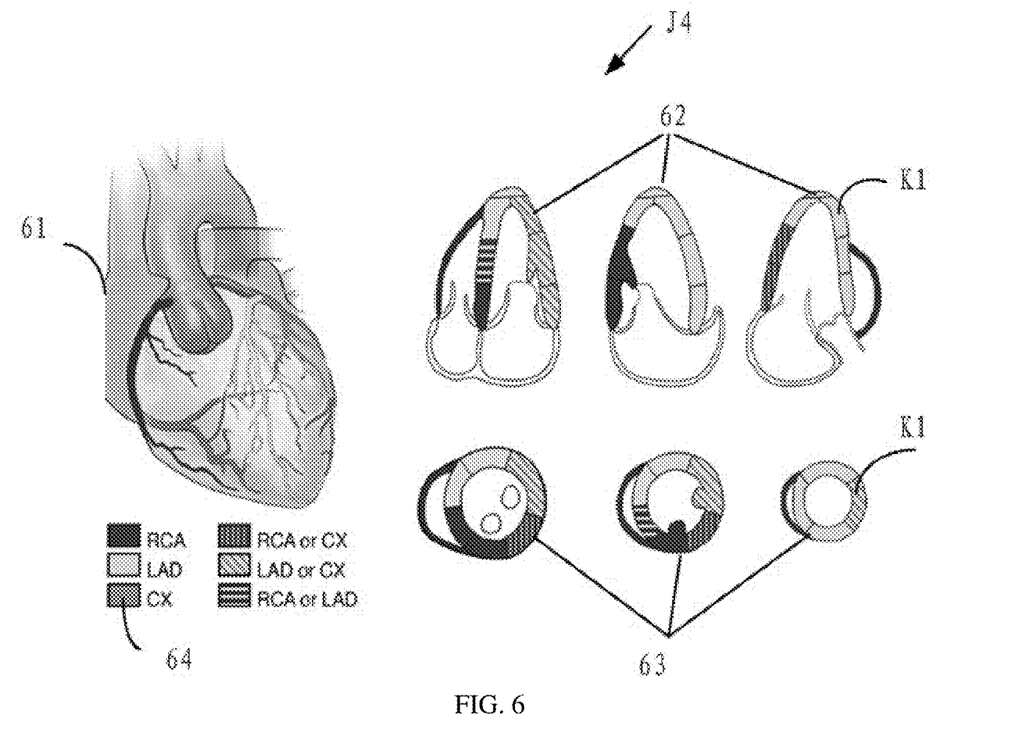
FIG. 6 is a schematic diagram of a health prompt interface in an embodiment of the disclosure.

In an embodiment, the anatomical shape formed by arranging the tracking quality indicators of the plurality of local sub-regions may be a shape of a cardiac segmented diagram (as shown in FIG. 3, FIG. 4, or FIG. 6) and/or a shape of a bull's eye plot (as shown in FIG. 5).

As shown in FIG. 3, more specifically, the process in which the processor 20 controls the display 10 to display the tracking quality of the at least one region of interest after the tracking is completed comprises: the display 10 is controlled to display the tracking determination interface J1 after the tracking is completed, wherein the tracking determination interface J1 comprises an ultrasound presentation playback zone Z1 and a tracking quality display zone Z2; the processor controls the ultrasound presentation to be displayed in the ultrasound presentation playback zone Z1 of the tracking determination interface J1; and the processor controls the tracking quality Q1 of the at least one region of interest to be displayed in the tracking quality display zone Z2 of the tracking determination interface J1.

The tracking determination interface J1 schematically shown in FIG. 3 displays the tracking quality of a region of interest, the ultrasound presentation playback zone Z1 is located in a middle position of the tracking determination interface J1, and the tracking quality display zone Z2 is located in a lower right corner region of the tracking determination interface J1.

The processor 20 also controls the addition of a corresponding marker B1 to the ultrasound presentation displayed in the ultrasound presentation playback zone Z1 according to the position and shape of the selected region of interest. For example, the marker B1 is a plurality of white scattered points distributed in an arched shape as shown in FIG. 3, and the distribution of the plurality of scattered points indicates the position and shape of the region of interest.

The tracking quality Q1 comprises tracking quality indicators G1 of a plurality of local sub-regions arranged in the anatomical shape of the region of interest in the form of color coding, and the quality standard reference indicator S1. Each local sub-region is associated with a corresponding tracking quality indicator G1 and a corresponding color coded block K1.

As shown in FIG. 3, in some embodiments, the tracking quality indicator G1 for each local sub-region is a contour line surrounding the corresponding color coded block K1, the contour line has a particular color, and the color of the contour line is different in shade when the local sub-regions have different tracking qualities. The quality standard reference indicator S1 displays the same color as the contour line, with the shades of the colors arranged in sequence and corresponding to different degrees of confidence. For example, as shown in FIG. 3, the quality standard reference indicator S1 corresponds to the degrees of confidence 0-100 respectively based on color changes from light to dark. Since the colors and shades of colors required by the drawings of the application document cannot be displayed more accurately, the drawings of the application are merely used as a reference and are specifically subject to the description.

The processor 20 displays the contour line having the corresponding shade of the color around the corresponding color coded block K1 according to the determined tracking quality of each local sub-region.

Thus, the user can determine the tracking quality, that is, the confidence, of the local sub-region corresponding to the color coded block K1 according to the shade of the color of the contour line of the color coded block K1 versus the quality standard reference indicator S1. For example, when the shade of the color of the contour line of a certain color coded block K1 is the same as the shade at a position 80 of the quality standard reference indicator S1, it can be determined that the confidence of the local sub-region corresponding to the color coded block K1 is 80%. That is, the credibility of the tracking result of the corresponding local sub-region is 80%.

Furthermore, each color coded block K1 has a different color to distinguish different local sub-regions.

In other embodiments, the tracking quality indicator G1 may be a texture pattern filled in the color coded block K1. The quality standard reference indicator S1 comprises a plurality of texture patterns, and different texture patterns correspond to different degrees of confidence.

The processor 20 displays the corresponding texture pattern in the corresponding color coded block K1 according to the determined tracking quality of each local sub-region.

Thus, the user can determine the tracking quality, that is, the confidence, of the local sub-region corresponding to the color coded block K1 according to the texture pattern in the color coded block K1 versus the quality standard reference indicator S1.

In other embodiments, the tracking quality indicator G1 may be the shade of the color of the color coded block K1. The quality standard reference indicator S1 comprises the relationship between the shade of the color and the confidence for each of a plurality of color coded block K1.

The processor 20 changes accordingly in controlling the shade of the color of the corresponding color coded block K1 according to the determined tracking quality of each local sub-region. Thus, the user can determine the tracking quality of the local sub-region corresponding to the color coded block K1 according to the shade of the color of the color coded block K1 versus the quality standard reference indicator S1.

The ultrasound presentation displayed in the ultrasound presentation playback zone Z1 of the tracking determination interface J1 in FIG. 3 is associated with the tracking quality Q1 displayed in the tracking quality display zone Z2, and the tracking quality Q1 changes as a picture of the ultrasound presentation changes, so that the displayed tracking quality Q1 is the tracking quality Q1 of the region of interest corresponding to the current picture of the ultrasound presentation.

As shown in FIG. 1, the ultrasound image processing device further comprises an input unit 50, and the processor 20 is further configured to discard an analysis result of one or more local sub-regions in response to an action of deleting the local sub-region that is inputted by the user through the input unit 50.

In some embodiments, the processor 20 is further configured to control the display 10 to generate a prompt message to prompt the user whether to accept this tracking result; if the user selects "Yes", the display 10 is controlled to display all analysis results.

Specifically, the process in which the processor 20 controls the all analysis results to be displayed on the display 10 comprises: the display 10 is controlled to display an analysis result interface and a bull's eye plot display interface simultaneously or alternately.

Referring also to FIG. 4, a schematic diagram of an analysis result interface J2 is shown. As shown in FIG. 4, the analysis result interface J2 comprises an ultrasound presentation playback zone Z21, an analysis curve display zone Z23 and a tracking quality display zone Z22, wherein the analysis curve display zone Z23 is configured to display a tracking result curve X1 of each local sub-region of the at least one region of interest; the ultrasound presentation playback zone Z21 of the analysis result interface is configured to display an ultrasound presentation; and the tracking quality display zone Z22 of the analysis result interface J2 is configured to display the tracking quality of the at least one region of interest.

In contrast to FIG. 3, the analysis result interface J2 displayed after the user selects to accept the analysis results will additionally display the tracking result curve X1 of each local sub-region.

The analysis curve display zone Z23 may be located at a lower left corner of the analysis result interface J2.

The ultrasound presentation playback zone Z21 and the tracking quality display zone Z23 in the analysis result interface J2 are the same as the ultrasound presentation playback zone Z1 and the tracking quality display zone Z2 in the tracking determination interface J1, and particular reference to the relevant descriptions of the ultrasound presentation playback zone Z1 and the tracking quality display zone Z2 in the tracking determination interface J1 are not repeated herein.

Likewise, the ultrasound presentation displayed in the ultrasound presentation playback zone Z21 of the analysis result interface J2 in FIG. 4 is associated in real time with the tracking quality Q1 displayed in the tracking quality display zone Z22 and the tracking result curve X1 displayed in the analysis curve display zone Z23, and the tracking quality Q1 and the tracking result curve X1 change as the picture of the displayed ultrasound presentation changes, so that the displayed tracking quality Q1 and the tracking result curve X1 are the tracking quality Q1 and the tracking result curve X1 of the region of interest corresponding to the current picture of the ultrasound presentation.

Referring also to FIG. 5, a schematic diagram of a bull's eye plot display interface J3 is shown. The bull's eye plot display interface J3 comprises a tracking result bull's eye plot display zone Z31, a tracking quality bull's eye plot display zone Z32 and a tracking time bull's eye plot display zone Z33, wherein the tracking result bull's eye plot display zone Z31 is configured to display a tracking result bull's eye plot T1 of at least one region of interest, the tracking quality bull's eye plot display zone Z32 is configured to display a tracking quality bull's eye plot T2 of at least one region of interest, and the tracking quality bull's eye plot display zone Z32 is configured to display a tracking time bull's eye plot T3 of at least one region of interest.

The tracking result bull's eye plot T1, the tracking quality bull's eye plot T2 and the tracking time bull's eye plot T2 corresponding to the at least one region of interest are simultaneously or alternately displayed.

Each tracking result bull's eye plot T1 is composed of a peak value of a tracking result of at least one local sub-region of tangent planes of the corresponding region of interest in a plurality of directions by the processor 20, each tracking quality bull's eye plot T2 is composed of a tracking quality of the peak value of the tracking result of at least one local sub-region of the tangent planes of the corresponding region of interest in a plurality of directions by the processor 20, and each tracking time bull's eye plot T3 is composed of the time at which the tracking result of at least one local sub-region of the tangent planes of the corresponding region of interest in a plurality of directions reaches the peak value by the processor 20.

For example, as shown in FIG. 5, the tracking result bull's eye plot T1 comprises a circular bull's eye plot composed of a result data block K2 formed by arranging, in a first preset direction D1, peak values of the tracking results of a plurality of local sub-regions of the tangent plane in a first direction, a result data block K2 formed by arranging, in a second preset direction D2, peak values of the tracking results of a plurality of local sub-regions of the tangent plane in a second direction, and a result data block K2 formed by arranging, in a third preset direction D3, peak values of the tracking results of a plurality of local sub-regions of the tangent plane in a third direction.

The tracking quality bull's eye plot T1 comprises a circular bull's eye plot K3 composed of a quality data block K3 formed by arranging, in the first preset direction, tracking qualities of the peak values of the tracking results of the plurality of local sub-regions of the tangent plane in the first direction, a data block K3 formed by arranging, in the second preset direction, tracking qualities of the peak values of the tracking results of the plurality of local sub-regions of the tangent plane in the second direction, and a data block formed by arranging, in the third preset direction, tracking qualities of the peak values of the tracking results of the plurality of local sub-regions of the tangent plane in the third direction.

The tracking time bull's eye plot T1 comprises a circular bull's eye plot K3 composed of a time data block K4 formed by arranging, in the first preset direction, time points when the tracking results of the plurality of local sub-regions of the tangent plane in the first direction reach the peak values, a time data block K4 formed by arranging, in the second preset direction, time points when the tracking results of the plurality of local sub-regions of the tangent plane in the second direction reach the peak values, and a time data block K4 formed by arranging, in the first preset direction, time points when the tracking results of the plurality of local sub-regions of the tangent plane in the third direction reach the peak values.

Therefore, in the form of the bull's eye plots, the peak values of the tracking results of the local sub-regions of the tangent planes in the plurality of directions, the qualities of the peak values of the tracking results and the time points when the tracking results reach the peak values can be visually and simultaneously illustrated.

The processor 20 is further configured to highlight the parts corresponding to local sub-regions of a target region of interest in the bull's eye plot in response to the local sub-regions of the target region of interest selected by the user.

For example, if the user wants to pay close attention to a certain local sub-region of a certain region of interest, the processor 20 can control the data blocks corresponding to the local sub-region in the tracking result bull's eye plot T1, the tracking quality bull's eye plot T2, and the tracking time bull's eye plot T3 for highlighting, by implementing the selection of the concerned local sub-region. For example, highlighting or displaying in different colors is performed.

The at least one region of interest comprises at least one of an endocardium, a midmyocardium, and an epicardium. The local sub-regions divided in advance are various regions divided according to functional tissues of the region of interest or user-defined regions selected by the user.

When the region of interest is the midmyocardium, the local sub-regions divided in advance are myocardial segments of the midmyocardium that are defined according to industry standards.

In some embodiments, the at least one region of interest comprises a midmyocardium, the midmyocardium comprises a plurality of myocardial segments, and at least one myocardial segment corresponds to a perfusion region of a coronary artery branch respectively; the processor 20 is further configured to highlight the parts corresponding to one or more myocardial segments in the tracking result bull's eye plot T1, the tracking quality bull's eye plot T2, and the tracking time bull's eye plot T3 corresponding to the midmyocardium according to a user selection or automatically; and the one or more myocardial segments correspond to perfusion regions of one or more designated coronary artery branches.

Referring also to FIG. 6, it is a schematic diagram of a health prompt interface J4 shown when the region of interest is the midmyocardium. In some embodiments, the processor 20 is further configured to provide the health prompt interface J4. For example, the processor 20 provides the health prompt interface J4 when the region of interest selected by the user is the midmyocardium and it is found that the coronary artery branches reflected by the myocardial segments of the midmyocardium have a health problem.

The health prompt interface J4 comprises a simulated heart icon 61, a plurality of physical simulated indication icons 62, a plurality of simplified indication icons 63, and a plurality of reference icons 64.

The simulated heart icon 61 simulates an overall structure of the heart. The plurality of physical simulated indication icons 62 are configured to illustrate the distribution of the myocardial segments in the same form as a distribution structure of the midmyocardium of the heart.

The plurality of simplified indication icons 63 illustrate the distribution of the myocardial segments in a simplified manner. As shown in FIG. 6, different myocardial segments are distinguished using color coded blocks K1 having different texture patterns.

The plurality of reference icons 64 illustrate coronary artery branches with their texture patterns corresponding to the myocardial segments, so that the user can determine, by reference, which coronary artery branch a myocardial segment having a certain texture pattern corresponds to.

The color coded block K1 corresponding to each myocardial segment is displayed in an arrangement shape consistent with the myocardial segment. The processor 20 may control the color coded block K1 corresponding to a certain myocardial segment to be highlighted when a tracking result of the myocardial segment shows that the corresponding coronary artery perfusion region could be diseased or has a poor function.

The tracking result of the application includes at least a quantitative parameter of myocardial motion.

The display 10 may be a built-in display or an external display of the ultrasound image processing device 100, such as an LCD display, an OLED display, a television, a mobile phone with a display screen, and a tablet computer. The processor 20 may be a central processor, a digital signal processor, a single chip microcomputer, a microprocessor, a microcontroller, etc. The memory 40 may be a flash memory card, a hard disk, an optical disk, etc. The input unit 50 may be a mouse, a touch screen, a touch pad, etc.

In the application, the confidence of the tracking results may be objectively reflected through the quantified tracking qualities. In addition, the tracking qualities may be illustrated vividly and displayed more visually according to the anatomical structure.

Figure 7:
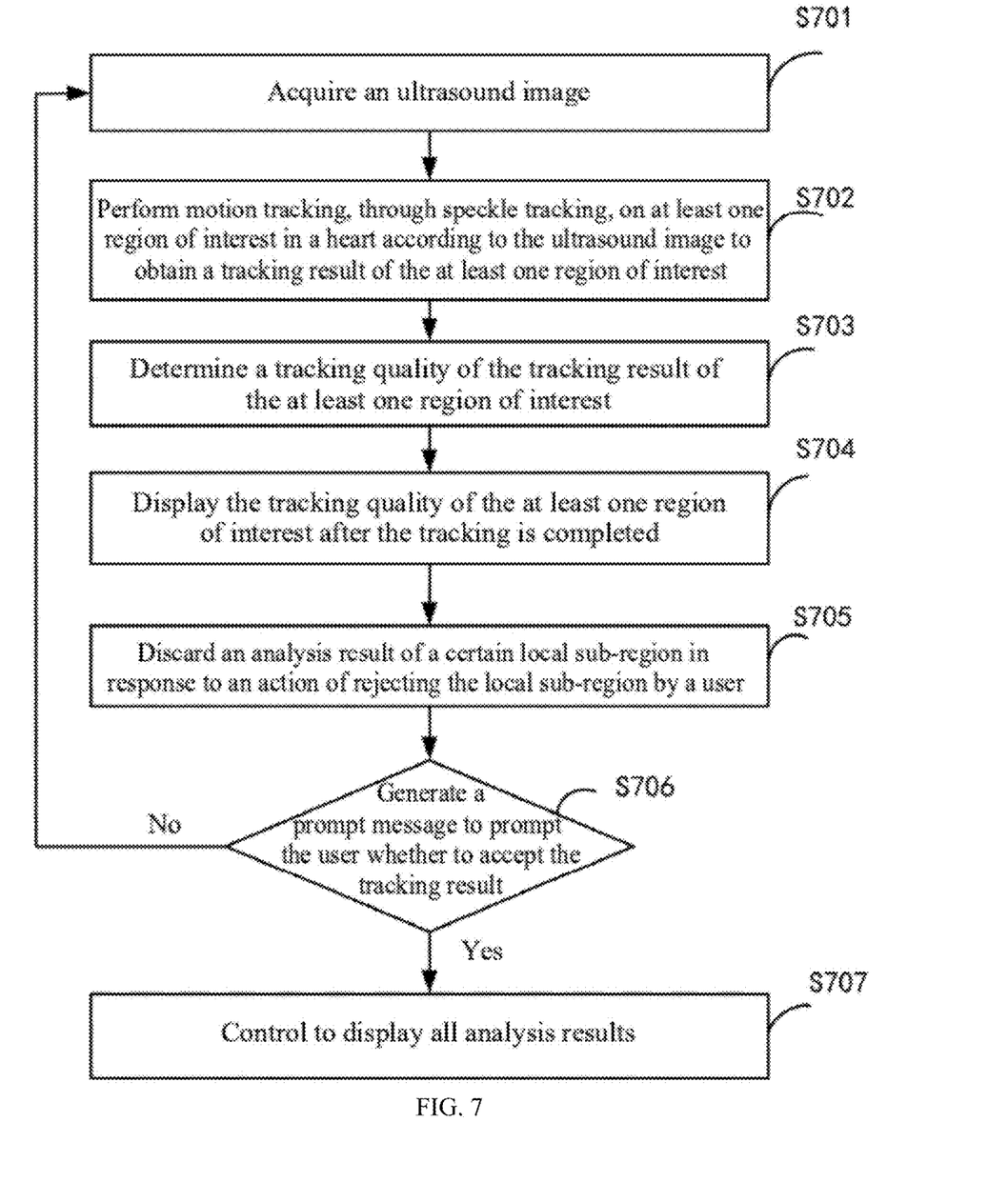
FIG. 7 is a flow chart of a method for quantitative analysis of cardiac motion in an embodiment of the disclosure.

Referring to FIG. 7, a flow chart of a method for quantitative analysis of cardiac motion in an embodiment of the disclosure is shown. The execution sequence of the steps of the flow chart in FIG. 7 may be optionally changed as required. The method for quantitative analysis of cardiac motion may be applied to the ultrasound image processing device 100, and for the hardware support for the steps of the method for quantitative analysis of cardiac motion, reference is made to the description of the ultrasound image processing device 100. As shown in FIG. 7, the method comprises the following steps.

An ultrasound presentation is acquired, wherein the ultrasound presentation comprises either one of an ultrasound image and an ultrasound video (S701). The step of acquiring the ultrasound presentation comprises: an ultrasound presentation is collected and acquired in real time by an ultrasound image processing device, or the ultrasound presentation collected and stored in advance is acquired from a memory or other device. Also, the ultrasound presentation is obtained by performing ultrasound scanning on at least one region of interest.

Motion tracking is performed, through speckle tracking, on at least one region of interest in a heart according to the ultrasound presentation to obtain a tracking result of the at least one region of interest (S702).

The tracking quality of the tracking result of the at least one region of interest is determined (S703). Specifically, the step S703 comprises: the tracking quality of each local sub-region of each region of interest is determined according to a plurality of local sub-regions formed by dividing each region of interest in advance.

After the tracking is completed, the tracking quality of the at least one region of interest is displayed, wherein the tracking quality is the confidence of a tracking result of a corresponding region of interest, indicating the credibility of the tracking result of the corresponding region of interest (S704).

Accordingly, in the application, what is determined and displayed according to the tracking result is the confidence of the tracking result, not just a simple qualified or unqualified determination result, so that the user can determine more accurately whether the tracking result is qualified or unqualified according to other factors.

As shown in FIG. 7, in some embodiments, the method further comprises a step: an analysis result of a certain local sub-region is discarded in response to an action of deleting the local sub-region by the user (S705).

As shown in FIG. 7, in some embodiments, the method further comprises a step: a prompt message is generated to prompt the user whether to accept the tracking result (S706).

If the user selects "Yes", all analysis results are controlled to be displayed (S707). If not, step S701 is repeated or the flow ends. In some embodiments, the step that "all analysis results are controlled to be displayed" comprises: an analysis result interface and a bull's eye plot display interface are controlled to be displayed simultaneously or alternately.

The analysis result interface comprises an ultrasound presentation playback zone, an analysis curve display zone and a tracking quality display zone, wherein the analysis curve display zone is configured to display a result curve of each local sub-region of the at least one region of interest; the ultrasound presentation playback zone of the analysis result interface is configured to display an ultrasound presentation; and the tracking quality display zone of the analysis result interface is configured to display the tracking quality of the at least one region of interest.

The bull's eye plot display interface comprises a tracking result bull's eye plot display zone, a tracking quality bull's eye plot display zone and a tracking time bull's eye plot display zone, wherein the tracking result bull's eye plot display zone is configured to display a tracking result bull's eye plot of at least one region of interest, the tracking quality bull's eye plot is configured to display a tracking quality bull's eye plot of at least one region of interest, and the tracking time bull's eye plot is configured to display a tracking time bull's eye plot of at least one region of interest.

In some embodiments, the tracking result bull's eye plot, the tracking quality bull's eye plot and the tracking time bull's eye plot corresponding to the at least one region of interest are simultaneously or alternately displayed.

Each tracking result bull's eye plot is composed of a peak value of a tracking result of at least one local sub-region of tangent planes of the corresponding region of interest in a plurality of directions, each tracking quality bull's eye plot is composed of a tracking quality of the peak value of the tracking result of at least one local sub-region of the tangent planes of the corresponding region of interest in a plurality of directions, and each tracking time bull's eye plot is composed of the time at which the tracking result of at least one local sub-region of the tangent planes of the corresponding region of interest in a plurality of directions reaches the peak value.

For a detailed introduction of the analysis result interface, the bull's eye plot display interface, the tracking result bull's eye plot, the tracking quality bull's eye plot, and the tracking time bull's eye plot, reference is made to the foregoing description, which will not be described in detail herein.

As shown in FIG. 7, in some embodiments, the method further comprises a step: the parts corresponding to local sub-regions of a target region of interest in the bull's eye plot are highlighted in response to the local sub-regions of the target region of interest selected by the user (S708).

In some embodiments, the at least one region of interest comprises a midmyocardium, the midmyocardium comprises a plurality of myocardial segments, and at least one myocardial segment corresponds to a perfusion region of a coronary artery branch respectively. The method further comprises a step: the parts corresponding to one or more myocardial segments in the bull's eye plots corresponding to the midmyocardium are highlighted according to the user selection or automatically, the one or more myocardial segments corresponding to perfusion regions of one or more designated coronary artery branches.

In some embodiments, the at least one region of interest comprises at least one of an endocardium, a midmyocardium, and an epicardium. The local sub-regions divided in advance are various regions divided according to functional tissues of the region of interest or user-defined regions selected by the user.

In some embodiments, when the region of interest is the midmyocardium, the local sub-regions divided in advance are myocardial segments of the midmyocardium that are defined according to industry standards.

Figure 8:
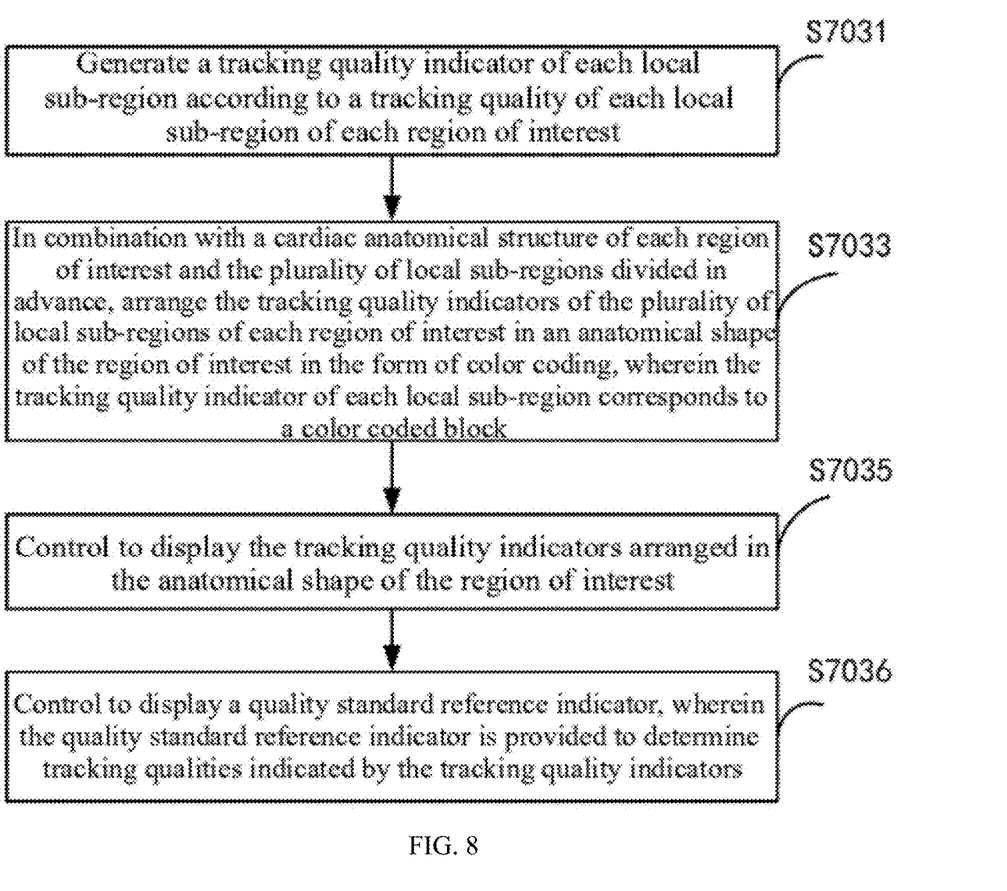
FIG. 8 is a sub-flow chart of step S703 in FIG. 7 in an embodiment.

Referring to FIG. 8, a sub-flow chart of step S703 in some embodiments is shown. As shown in FIG. 8, the step S703 comprises the following steps.

A tracking quality indicator of each local sub-region is generated according to a tracking quality of each local sub-region of each region of interest (S7031).

In combination with a cardiac anatomical structure of each region of interest and the plurality of local sub-regions divided in advance, the tracking quality indicators of the plurality of local sub-regions of each region of interest are arranged in an anatomical shape of the region of interest in the form of color coding, wherein the tracking quality indicator of each local sub-region corresponds to a color coded block (S7033).

The tracking quality indicators arranged in the anatomical shape of the region of interest are controlled to be displayed (S7035). In addition, a quality standard reference indicator is controlled to be displayed, wherein the quality standard reference indicator is provided to determine tracking qualities indicated by the tracking quality indicators (S7036).

In some embodiments, the step S703 may further comprise: a tracking determination interface is displayed after the tracking is completed, wherein the tracking determination interface comprises an ultrasound presentation playback zone and a tracking quality display zone; the ultrasound presentation is displayed in the ultrasound presentation playback zone of the tracking determination interface; and the tracking quality of the at least one region of interest is displayed in the tracking quality display zone of the tracking determination interface.

In some embodiments, the application also provides a computer-readable storage medium. The computer-readable storage medium stores a plurality of program instructions to be invoked for execution by the processor 20. The computer-readable storage medium may be the memory 40.

After a plurality of program instructions stored in the memory 40/computer-readable storage medium are invoked for execution by the processor 20, some or all of the steps of the method illustrated in either one of FIGS. 7 and 8, or any combination thereof may be executed.

Therefore, by providing the confidence of the tracking results, the application may allow the user to know the credibility of the tracking results and analyze more accurately whether the tracking results are qualified or unqualified according to other factors, and the application may also more visually display the tracking qualities with corresponding shapes according to the structural shape of the region of interest.

The description has been made with reference to various exemplary embodiments herein. However, those skilled in the art would have appreciated that changes and modifications could have been made to the exemplary embodiments without departing from the scope herein. For example, various operation steps and assemblies for executing operation steps may be implemented in different ways according to a specific application or considering any number of cost functions associated with the operation of the system (for example, one or more steps may be deleted, modified or incorporated into other steps).

In addition, as understood by those skilled in the art, the principles herein may be reflected in a computer program product on a computer-readable storage medium that is pre-installed with computer-readable program codes. Any tangible, non-transitory computer-readable storage medium can be used, including magnetic storage devices (hard disks, floppy disks, etc.), optical storage devices (CD-ROM, DVD, Blu Ray disks, etc.), flash memories, and/or the like. These computer program instructions can be loaded onto a general-purpose computer, a dedicated computer, or other programmable data processing device to form a machine, such that these instructions executed on a computer or other programmable data processing apparatus can generate an apparatus that implements a specified function. These computer program instructions can also be stored in a computer-readable memory that can instruct a computer or other programmable data processing device to operate in a specific manner, such that the instructions stored in the computer-readable memory can form a manufactured product, including an implementation apparatus that implements a specified function. The computer program instructions can also be loaded onto a computer or other programmable data processing device, such that a series of operating steps are executed on the computer or other programmable device to produce a computer-implemented process, such that the instructions executed on the computer or other programmable device can provide steps for implementing a specified function.

Although the principles herein have been shown in various embodiments, many modifications of structures, arrangements, ratios, elements, materials, and components that are particularly suitable for specific environments and operating requirements can be made without departing from the principles and scope of the disclosure. The above modifications and other changes or amendments will be included within the scope herein.

The above specific description has been described with reference to various embodiments. However, those skilled in the art would have appreciated that various modifications and changes could have been made without departing from the scope of the disclosure. Therefore, consideration of the disclosure will be in an illustrative rather than a restrictive sense, and all such modifications will be included within the scope thereof. Likewise, the advantages of various embodiments, other advantages, and the solutions to problems have been described above. However, the benefits, advantages, solutions to problems, and any elements that can produce these, or solutions that make them more explicit, should not be interpreted as critical, necessary, or essential. The term "comprising" and any other variants thereof used herein are non-exclusive, such that the process, method, document, or device that includes a list of elements includes not only these elements, but also other elements that are not explicitly listed or do not belong to the process, method, system, document, or device. Furthermore, the term "coupling" and any other variations thereof used herein refer to physical connection, electrical connection, magnetic connection, optical connection, communication connection, functional connection, and/or any other connection.

Those skilled in the art will recognize that many changes can be made to the details of the above-described embodiments without departing from the basic principles of the disclosure. Therefore, the scope of the disclosure should be determined only by the claims as follows.

The invention claimed is:

1. An ultrasound image processing device for quantitative analysis of cardiac motion, comprising:
   a display; and
   a processor configured to:
   obtain an ultrasound presentation, wherein the ultrasound presentation comprises one of an ultrasound image and an ultrasound video;
   perform a motion tracking on at least one region of interest in a myocardial tissue according to the ultrasound presentation to obtain tracking results of a plurality of local sub-regions formed by dividing the at least one region of interest;
   determine confidence values of the tracking results of the plurality of local sub-regions of the at least one region of interest as tracking qualities of the tracking results;
   control the display to display the confidence values of the tracking results of the plurality of local sub-regions of the at least one region of interest;
   generate tracking quality indicators of the plurality of local sub-regions according to the tracking qualities of the tracking results of the plurality of local sub-regions, wherein each of the plurality of local sub-regions has a respective tracking quality indicator;
   arrange the tracking quality indicators of the plurality of local sub-regions of the region of interest in an anatomical shape of the region of interest in a form of color coding according to an anatomical structure of the region of interest and the plurality of local sub-regions, wherein each of the plurality of local sub-regions corresponds to a color coded block, and different local sub-regions correspond to color coded blocks with different colors, wherein:
   the tracking quality indicator of each local sub-region is represented by a shade of a color of a contour line surrounding the corresponding color coded block, and different shades of the color correspond to different confidence values; or
   the tracking quality indicator of each local sub-region is represented by a texture pattern filled in the corresponding color coded block, and different texture patterns correspond to different confidence values; and
   control the display to display the tracking quality indicators arranged in the anatomical shape of the region of interest.

2. The ultrasound image processing device of claim 1, wherein the processor is further configured to:
   control the display to display a quality standard reference indicator, wherein the quality standard reference indicator is used for determining the tracking qualities indicated by the tracking quality indicators.

3. The ultrasound image processing device of claim 1, further comprising an input unit, wherein the processor is further configured to, in response to an action of deleting one or more local sub-regions that is input by a user through the input unit, discard an analysis result, comprising one or more tracking results, of the deleted one or more local sub-regions.

4. The ultrasound image processing device of claim 1, wherein the processor is further configured to:
   generate a prompt message to prompt a user whether to accept the tracking results of the plurality of local sub-regions and control the display to display the prompt message; and
   control the display to display an analysis result comprising the tracking results of the plurality of local sub-regions when the user accepts the tracking results.

5. The ultrasound image processing device of claim 1, wherein the anatomical shape formed by arranging the tracking quality indicators of the plurality of local sub-regions is a shape of a cardiac segmented diagram and/or a shape of a bull's eye plot.

6. The ultrasound image processing device of claim 5, wherein the processor is further configured to:
   in response to selecting a local sub-region of the plurality of local sub-regions of the at least one region of interest by a user, highlight a part of the anatomical shape corresponding to the selected local sub-region.

7. The ultrasound image processing device of claim 1, wherein each of the tracking results comprises at least a quantitative parameter of myocardial motion.

8. The ultrasound image processing device of claim 1, further comprising a memory, wherein the processor is configured to obtain, from the memory, the ultrasound presentation that is collected and stored in advance.

9. The ultrasound image processing device of claim 1, further comprising an ultrasound presentation collecting apparatus configured to collect the ultrasound presentation, wherein the processor is configured to obtain the ultrasound presentation collected by the ultrasound presentation collecting apparatus.

10. The ultrasound image processing device of claim 9, wherein the ultrasound presentation collecting apparatus comprises:
    a probe;

a transmitting circuit configured to excite the probe to transmit an ultrasound wave to the region of interest; and a receiving circuit configured to receive echoes of the ultrasound wave to obtain echo signals;

wherein the processor is configured to process the echo signals to obtain the ultrasound presentation.

11. The ultrasound image processing device of claim 1, wherein the at least one region of interest comprises at least one of an endocardium, a midmyocardium and an epicardium.

12. An ultrasound image processing method for quantitative analysis of cardiac motion, comprising:

obtaining an ultrasound presentation, wherein the ultrasound presentation comprises one of an ultrasound image and an ultrasound video;

performing a motion tracking on at least one region of interest in a myocardial tissue according to the ultrasound presentation to obtain tracking results of a plurality of local sub-regions formed by dividing the at least one region of interest;

determining confidence values of the tracking results of the plurality of local sub-regions of the at least one region of interest as tracking qualities of the tracking results; and displaying the confidence values of the tracking results of the plurality of local sub-regions of the at least one region of interest, wherein displaying the confidence values of the tracking results of the plurality of local sub-regions of the at least one region of interest comprises:

generating tracking quality indicators of the plurality of local sub-regions according to the tracking qualities of the tracking results of the plurality of local sub-regions, wherein each of the plurality of local sub-regions has a respective tracking quality indicator;

arranging the tracking quality indicators of the plurality of local sub-regions of the region of interest in an anatomical shape of the region of interest in a form of color coding according to an anatomical structure of the region of interest and the plurality of local sub-regions, wherein each of the plurality of local sub-regions corresponds to a color coded block, and different local sub-regions correspond to color coded blocks with different colors, wherein:

the tracking quality indicator of each local sub-region is represented by a shade of a color of a contour line surrounding the corresponding color coded block, and different shades of the color correspond to different confidence values; or the tracking quality indicator of each local sub-region is represented by a texture pattern filled in the corresponding color coded block, and different texture patterns correspond to different confidence values; and displaying the tracking quality indicators arranged in the anatomical shape of the region of interest.

13. The ultrasound image processing method of claim 12, wherein displaying the confidence values of the tracking results of the plurality of local sub-regions of the at least one region of interest further comprises:

displaying a quality standard reference indicator, wherein the quality standard reference indicator is used for determining the tracking qualities indicated by the tracking quality indicators.

14. The ultrasound image processing method of claim 12, further comprising:

in response to an action of deleting one or more local sub-region by a user, discarding an analysis result, comprising one or more tracking results, of the deleted one or more local sub-regions.

15. The ultrasound image processing method of claim 12, further comprising:

generating a prompt message to prompt a user whether to accept the tracking results of the plurality of local sub-regions and displaying the prompt message; and displaying an analysis result comprising the tracking results of the plurality of local sub-regions when the user accepts the tracking results.

16. A non-transitory computer-readable storage medium for quantitative analysis of cardiac motion, wherein the non-transitory computer-readable storage medium stores a plurality of program instructions, and the plurality of program instructions are executed by a processor to cause the processor to:

obtain an ultrasound presentation, wherein the ultrasound presentation comprises one of an ultrasound image and an ultrasound video;

perform a motion tracking on at least one region of interest in a myocardial tissue according to the ultrasound presentation to obtain tracking results of a plurality of local sub-regions formed by dividing the at least one region of interest;

determine confidence values of the tracking results of the plurality of local sub-regions of the at least one region of interest as tracking qualities of the tracking results;

control a display to display the confidence values of the tracking results of the plurality of local sub-regions of the at least one region of interest;

generate tracking quality indicators of the plurality of local sub-regions according to the tracking qualities of the tracking results of the plurality of local sub-regions, wherein each of the plurality of local sub-regions has a respective tracking quality indicator;

arrange the tracking quality indicators of the plurality of local sub-regions of the region of interest in an anatomical shape of the region of interest in a form of color coding according to an anatomical structure of the region of interest and the plurality of local sub-regions, wherein each of the plurality of local sub-regions corresponds to a color coded block, and different local sub-regions correspond to color coded blocks with different colors, wherein:

the tracking quality indicator of each local sub-region is represented by a shade of a color of a contour line surrounding the corresponding color coded block, and different shades of the color correspond to different confidence values; or the tracking quality indicator of each local sub-region is represented by a texture pattern filled in the corresponding color coded block, and different texture patterns correspond to different confidence values; and control the display to display the tracking quality indicators arranged in the anatomical shape of the region of interest.

* * * * *